United States Patent [19]

Hutchinson

[11] Patent Number: 4,767,628

[45] Date of Patent: Aug. 30, 1988

[54] CONTINUOUS RELEASE PHARMACEUTICAL COMPOSITIONS

[75] Inventor: Francis G. Hutchinson, Lymm, United Kingdom

[73] Assignee: Imperial Chemical Industries PLC, London, England

[21] Appl. No.: 68,760

[22] Filed: Jun. 29, 1987

Related U.S. Application Data

[63] Continuation of Ser. No. 640,855, Aug. 15, 1984, abandoned, which is a continuation of Ser. No. 344,722, Feb. 1, 1982, abandoned.

[30] Foreign Application Priority Data

Feb. 16, 1981 [GB] United Kingdom ............... 8104734

[51] Int. Cl.$^4$ ........................... A61K 9/26; A61K 9/32
[52] U.S. Cl. ..................... 424/426; 514/12; 514/13; 514/14; 514/15
[58] Field of Search ..................... 514/12–15; 424/422, 423, 426

[56] References Cited

U.S. PATENT DOCUMENTS

| | | | |
|---|---|---|---|
| 3,773,919 | 11/1973 | Boswell et al. | 424/78 |
| 3,887,699 | 6/1975 | Yolles | 424/78 |
| 3,976,071 | 8/1976 | Sadek | 424/423 |
| 4,331,652 | 5/1982 | Ludwig et al. | 424/78 |
| 4,333,919 | 6/1982 | Kleber et al. | 424/78 |

FOREIGN PATENT DOCUMENTS 1325209 8/1973 United Kingdom .

*Primary Examiner*—J. R. Brown
*Assistant Examiner*—F. T. Moezie
*Attorney, Agent, or Firm*—Cushman, Darby & Cushman

[57] ABSTRACT

Pharmaceutical compositions, comprising a polylactide and a pharmacologically active, acid stable polypeptide, which when placed in an aqueous physiological environment release the polypeptide at an approximately constant rate in an essentially monophasic manner, with a minimal, or no induction period prior to the release; polylactides suitable for use in said compositions; and a method for the manufacture of such polylactides.

17 Claims, No Drawings

CONTINUOUS RELEASE PHARMACEUTICAL COMPOSITIONS

This is a continuation of application Ser. No. 640,855 filed Aug. 15, 1984 which was abandoned upon the filing hereof which in turn is a continuation of application Ser. No. 344,722 filed Feb. 1, 1982, both now abandoned.

This invention relates to pharmaceutical compositions of pharmacologically-active acid-stable polypeptides, which provide continuous release of the polypeptide over an extended period when the composition is placed in an aqueous, physiological-type environment.

It has long been appreciated that the continuous release of certain drugs over an extended period following a single administration could have significant practical advantages in clinical practice, and compositions have already been developed to provide extended release of a number of clinically useful drugs, after oral dosing (see, for example, Remington's Pharmaceutical Sciences, published by Mack Publishing Company, Easton, Penn., U.S.A., 15th Edition, 1975, pages 1618–1631), after parenteral administration (ibidem, pages 1631–1643), and after topical administration (see, for example, United Kingdom Patent No. 1,351,409). A suitable method of parenteral administration is the subdermal injection or implantation of a solid body, for example a pellet or a film, containing the drug, and a variety of such implantable devices has been described. In particular, it is known that, for many drugs, suitable implantable devices for providing extended drug release may be obtained by encapsulating the drug in a biodegradable polymer, or by dispersing the drug in a matrix of such a polymer, so that the drug is released as the degradation of the polymer matrix proceeds.

Suitable biodegradable polymers for use in sustained release formulations are well known, and include polyesters, which gradually become degraded by hydrolysis when placed in an aqueous, physiological-type environment. Particular polyesters which have been used are those derived from hydroxycarboxylic acids, and much prior art has been directed to polymers derived from α-hydroxycarboxylic acids, especially lactic acid in both its racemic and optically active forms, and glycolic acid, and copolymers thereof-see, for example, U.S. Pat. Nos. 3,773,919 and 3,887,699; Jackanicz et al., Contraception, 1973, 8, 227–234; Anderson et al., ibidem, 1976, 11, 375–384; Wise et al., Life Sciences, 1976, 19, 867–874; Woodland et al., Journal of Medicinal Chemistry, 1973, 16, 897–901; Yolles et al., Bulletin of the Parenteral Drug Association, 1976, 30, 306–312; Wise et al., Journal of Pharmacy and Pharmacology, 1978, 30, 686–689 and 1979, 31, 201–204.

In this specification, the term "polylactide" is used in a generic sense to include polymers of lactic acid alone, copolymers of lactic acid and glycolic acid, mixtures of such polymers, mixtures of such copolymers, and mixtures of such polymers and copolymers, the lactic acid being either in racemic or in optically active form. Also, the term "acid-stable" is to be understood as meaning that the polypeptide is not significantly hydrolysed under the conditions encountered within the claimed formulations during the period of use envisaged, that is, at pH 2 at mammalian body temperature, say up to 40°C., for up to six months.

United Kingdom Patent Specification No. 1,325,209 (equivalent to U.S. Pat. Specification No. 3,773,919) and U.S. Pat. Specification No. 3,887,669 is the only prior art known to us which makes any reference to extended or sustained release of polypeptides, the latter mentioning insulin only, but it contains no specific example of any such formulation, and the reference to polypeptides is apparently entirely speculative, appearing, as it does, only in an extensive listing of very many different classes of drugs which can allegedly be incorporated into formulations of the kind described therein. In fact, essentially all of the other drug types referred to in that specification, apart from polypeptides, are relatively hydrophobic in character and of relatively low molecular weight, and the disclosure of that specification displays no recognition of the difficulties which we have encountered when seeking to obtain satisfactory sustained release formulations of polypeptides, many of which are relatively hydrophilic, and of relatively high molecular weight.

It is to be appreciated that "sustained" or "extended" release of a drug may be either continuous or discontinuous. We have now discovered, in fact, that in many cases when the teaching of the prior art, and in particular the teaching of United Kingdom Specification No. 1,325,209, is applied to the manufacture of a formulation of an acid-stable polypeptide, the release of the polypeptide from the formulation, although occurring over an extended period of time, may also be discontinuous. For example, the release of a polypeptide from a polylactide polymer as described in the said Specification is often preceded by a significant induction period, during which no polypeptide is released, or is biphasic, and comprises an initial period during which some polypeptide is released, a second period during which little or no polypeptide is released, and a third period during which most of the remainder of the polypeptide is released. By contrast, it is an object of the present invention to provide compositions of acid-stable polypeptides from which, apart possibly from a relatively short initial induction period, the polypeptide is released continuously, with no periods during which little or no polypeptide is released. The words "continuous release" are used in this specification solely to describe a release profile which is essentially monophasic, although it may have a point of inflection, but certainly has no "plateau" phase.

Thus, according to the present invention, there is provided a pharmaceutical composition comprising a polylactide, as hereinbefore defined, and an acid-stable polypeptide, which, when placed in an aqueous physiological-type environment, releases polypeptide into said aqueous physiological-type environment in a continuous manner, as hereinbefore defined, until essentially all of the polypeptide has been released.

This invention is applicable to acid-stable polypeptides quite generally, without any limitation as to structure or molecular weight, but is most useful for polypeptides which are relatively hydrophilic, and the following list, which is not intended to be exhaustive, is indicative of polypeptides which may be employed in the formulation of this invention: oxytocin, vasopressin, adrenocorticotrophic hormone (ACTH), epidermal growth factor (EGF), prolactin, luliberin or luteinizing hormone releasing hormone (LH-RH), insulin, somatostatin, glucagon, interferon, gastrin, tetragastrin, pentagastrin, urogastrone, secretin, calcitonin, enkephalins, endorphins, angiotensins, renin, bradykinin, bacitracins polymyxins, colistins, tyrocidin, gramicidines, and synthetic analogues and modifications and pharmacologically-active fragments thereof.

We have found, however, that polypeptides which are not stable under acid conditions, are unsuitable for use in the compositions of this invention, as they become degraded in the acid environment produced in the polymer matrix when the polyactide starts to degrade by hydrolysis, thus producing carboxylic acid end groups.

By "an aqueous physiological-type environment" we mean the body, particularly the musculature or the circulatory system, of a warm-blooded animal, although in laboratory investigations such an environment may be mimicked by aqueous liquids, optionally buffered to a physiological pH, at a temperature of between 35° and 40° C.

The continuous release composition of the invention may be placed in the body of an animal which it is desired to treat with a polypeptide by, for example, intramuscular or subcutaneous injection, or by sub-dermal surgical implantation, in conventional clinical or veterinary manner.

We have discovered that a pharmaceutical composition according to the invention may be designed to provide continuous release of the polypeptide by the appropriate choice or control of various parameters, for example by varying the polylactide composition, particularly the proportion of lactic acid to glycolic acid in copolymers; by controlling the molecular weight of the polylactide, both the weight-average molecular weight, and the molecular weight range or polydispersity, measured by the ratio of the weight-average molecular weight, ($M_w$), to the number-average molecular weight ($M_n$), i.e. $M_w/M_n$; by choice of the proportion of polypeptide to polylactide; or by choice of the geometry of a solid formulation for implantation, or of the particle size in a formulation for injection. The release characteristics of such compositions are also controlled to some extent by the nature of the polypeptide itself. In particular, there is less freedom of choice in defining the parameters mentioned above when designing a composition of the invention for a polypeptide of high molecular weight, (say, greater than 6000), than there is when designing a composition for a polypeptide of lower molecular weight, (say, less than 6000).

We have further discovered that the release of a polypeptide from a composition comprising a polylactide and a polypeptide proceeds by two distinct and independent mechanisms, namely first a diffusion-dependent release of polypeptide out of the polylactide-polypeptide matrix comprising leaching from the surface, and, for low molecular weight polypeptides, some partition-dependent diffusion of polypeptide per se; and subsequently, as the polylactide becomes degraded, diffusion of aqueous polypeptide solution out of the composition through aqueous channels.

In general, the compatibility of polypeptides in polylactide polymers is limited, except in the case of low molecular weight (up to, say, 6000 molecular weight) polypeptides which are capable of having some specific interaction with the polylactide, for example a low molecular weight polypeptide which is basic, and which therefore interacts with the terminal carboxylic acid groups in the polylactide. Because of this limited compatibility of polypeptide in polylactide, a polypeptide/polylactide formulation, when placed in an aqueous environment, releases very little polypeptide by diffusion through the polymer matrix. While this is broadly true for all combinations of polypeptide and polylactide, matrix diffusion is at a minimum for high molecular weight polypeptides in high molecular weight polylactides. Even when some matrix diffusion resulting in polypeptide release occurs initially on placing the composition in an aqueous environment, by release from or very near the surface, this soon ceases because the diffusion of polypeptide into polylactide is insufficient to result in continuous transport of polypeptide from inside the composition to its surface.

When a polypeptide/polylactide composition is placed in an aqueous environment, water diffuses into the matrix, and is partitioned between polypeptide and polylactide to form domains of aqueous polypeptide solution. This aqueous polypeptide, obtained when absorbed water is partitioned between polypeptide and polylactide, is incompatible with, and insoluble in, polylactides, particularly those of high molecular weight, so that absorption of water by the composition still further reduces initially any likelihood of matrix diffusion of polypeptide out of the composition. If the aqueous domains of polypeptide so formed are discrete and isolated, then the compositions are incapable of releasing polypeptide. However, the possibility of the aqueous polypeptide domains having some continuity increases with increasing concentration of polypeptide in the composition, and with increasing absorption of water, and when the continuity of aqueous polypeptide domains reaches a sufficient level to communicate with the exterior surface of the composition, polypeptide starts to be released from the formulation by diffusion, not through the polylactide matrix, but through aqueous polypeptide channels. Even when some aqueous polypeptide domains near the surface have extended so as to reach the exterior of the composition, that aqueous polypeptide which exists in still isolated domains is not released, and is only released when a secondary hydrophilic path for diffusion becomes available. For high molecular weight polylactides, this secondary hydrophilic diffusion path arises when the polylactide has undergone sufficient degradation for the rate of absorption of water to increase significantly. When this occurs, aqueous pores or channels are generated in the polylactide matrix, which allow a continuous and significant release of polypeptide, as aqueous solution, from previously discrete and isolated domains.

As indicated above, we have discovered that, when sustained release compositions of the prior art, and particularly those described in United Kingdom Patent Specification No. 1,325,209, are used for the release of polypeptides, the initial matrix diffusion phase of polypeptide release, and the secondary release of polypeptide consequent upon degradation of the polylactide, are separated in time with the result that the release of polypeptide is not continuous, but is biphasic and discontinuous, comprising a small first release of polypeptide, a dead phase during which essentially no polypeptide is released, and a subsequent second release phase, during which substantially all of the remaining polypeptide is released. We have now discovered that, by appropriate choice of the parameters of the composition, the matrix diffusion phase of release, and the subsequent degradation induced phase of release, can be made to overlap in time.

Thus, according to a further feature of the invention there is provided a pharmaceutical composition comprising a polylactide, as hereinbefore defined, and an acid-stable polypeptide, and exhibiting two successive phases of release of polypeptide when placed in an aqueous physiological-type environment, the first phase being release by matrix diffusion and the second phase being release consequent upon degradation of the polyactide, characterised in that the diffusion phase and the degradation-induced phase overlap in time.

The two phases can be made to overlap by either extending the initial diffusion phase, or making the degradation-induced phase commence earlier, or both.

The initial matrix release phase is difficult to extend, but is sensitive to the concentration of the polypeptide in the matrix, and to a limited extent, to the nature of the polypeptide, especially its hydrophilicity, The degradation-induced release phase can be made to start sooner by appropriate choice of polylactide composition (more glycolide-rich polymer molecules, which degrade more quickly than lactide-rich molecules), $M_w$ (molecules of low molecular weight degrade more quickly to a level at which aqueous channels appear in the matrix), and polypeptide concentration (a higher polypeptide concentration allows more rapid absorption of water, and consequently more rapid generation of continuous aqueous channels which facilitate polypeptide release).

However, as well as requiring the degradation-induced release phase to start earlier, it is also necessary to control the rate of polypeptide release during this phase, and to ensure that the total duration of this phase is sufficient for its intended clinical or veterinary purpose. One method of extending the duration of the degradation-induced release phase, is to use polylactides which contain lactide-rich molecules, which degrade more slowly than glycolide-rich molecules, or alternatively, polylactides containing molecules of high molecular weight, which take longer to degrade to a level at which aqueous channels are formed, can be used.

It is apparent, therefore, that since glycolide-rich polymer molecules, and/or molecules of low molecular weight, are preferred if the degradation phase is to start quickly, and lactide-rich molecules, and/or molecules of high molecular weight are preferred if the degradation-induced release phase is to last for a sufficient period of time, preferred polylactides are those with a high degree of heterogeneity, in respect of glycolide-rich and lactide-rich molecules, or of high polydispersity.

Alternatively, the same characteristics can be obtained by blending two or more different polylactides, which differ in lactide/glycolide content, and/or in $M_w$. In addition, the blending of a minor proportion of polylactide of high $M_w$ with a polylactide of low $M_w$, confers desirable physical properties upon compositions according to this invention produced therefrom, making them easier to fabricate and process.

We have further discovered that the profile of polypeptide release from both prior art polylactides and novel polylactides is almost exactly parallelled by the profile of water absorption. That is to say, when polypeptide release is discontinuous, water absorption is also discontinuous in essentially the same manner, and conversely, when polypeptide release is continuous, so is water absorption. Furthermore, variation of the parameters referred to above for controlling the polypeptide release characteristics of the composition have been found to affect water absorption by the composition in an exactly parallel manner.

Thus, according to a further feature of the invention there is provided a pharmaceutical composition, comprising a polylactide as hereinbefore defined and an acid-stable polypeptide, which when placed in an aqueous physiological-type environment absorbs water in a continuous manner as hereinbefore defined, until the polylactide has been degraded and essentially all of the polypeptide has been released into said aqueous physiological-type environment.

The effect of the various parameters, referred to above, on the polypeptide release and/or water absorption characteristics of compositions of the invention is illustrated by the following experiments:

A. Molecular weight of the polylactide component

A.1. Low molecular weight polypeptide

A.1.1.Formulations were manufactured comprising 20% w/w of the gastric peptide fragment tetragastrin hydrochloride, Trp-Met-Asp-Phe-NH$_2$.HCl, molecular weight=633, in a polylactide comprising equimolar proportions of D,L-lactide and glycolide units, in the form of a film 0.2 mm. thick. The films were placed individually in water at 37° C., which was changed daily, and the ultraviolet absorption at 277 nm. was measured to assay the tetragastrin released by the formulation that day.

With a prior art type of polylactide of $M_w$ approximately 240,000 (intrinsic viscosity=1.36), there was an initial release of tetragastrin, then a "dead period" from about day 5 to day 21 during which little was released, followed by the main release from day 24 onward.

With a novel polylactide of $M_w$ approximately 15,000 (intrinsic viscosity=0.25), the release pattern was similar, but the dead period lasted only from day 4 or 5 to day 8 or 9.

With a novel polylactide of low $M_w$ (inherent viscosity of a 1 g./100 ml. solution in chloroform=0.11), there was no dead period, and tetragastrin was released continuously from time zero ($T_o$).

A.1.2. Similar formulations were manufactured using 10% by weight of the synthetic luliberin analogue ICI.118,630,

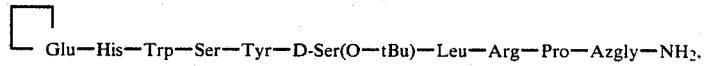
Glu—His—Trp—Ser—Tyr—D-Ser(O—tBu)—Leu—Arg—Pro—Azgly—NH$_2$.

molecular weight=1269, in place of tetragastrin.

With a prior art polylactide of $M_w \sim 240,000$ (intrinsic viscosity=1.36), the release of the polypeptide was biphasic, with a dead period of about 15 days.

With a novel polylactide of $M_w \sim 15,000$ (intrinsic viscosity=0.25), there was a short induction period, followed by continuous release.

With a novel polylactide of low $M_w$ (inherent viscosity of a 1 g./100 ml. solution in chloroform=0.11), there was continuous release from $T_o$.

A.2. Medium molecular weight polypeptide

Formulations were manufactured comprising 0.1% by weight of mouse epidermal growth factor (EGF), molecular weight=6041, in polylactides comprising equimolar proportions of D,L-lactic acid and glycolic acid units, and of different $M_w$, and placed in pH 7.4 buffer. Release of EGF was monitored by radio-immunoassay.

With a prior art polylactide of $M_w \sim 200{,}000$ (intrinsic viscosity=1.08), there was no initial release, and no significant release of polypeptide until between 13 and 20 days after $T_o$, after which release was continuous.

With a novel polylactide of $M_w \sim 80{,}000$ (intrinsic viscosity=0.58), there was also no initial release, and significant release did not occur until between 6 and 10 days after $T_o$, after which release was continuous.

With a novel polylactide of low $M_w$ (inherent viscosity of a 1 g./100 ml. solution in chloroform=0.11), there was continuous release from $T_o$.

A.3. High molecular weight polypeptide

A formulation was manufactured comprising 20% w/w of bovine prolactin, molecular weight ~22,000, in a novel polylactide comprising equimolar proportions of D,L-lactic acid and glycolic acid units, and of low $M_w$ (inherent viscosity of 1g./100ml. solution in chloroform=0.11). As expected from previous experiments A.1.1, A.1.2 and A.2, this formulation also released polypeptide continuously from $T_o$ when tested in vivo in rats, and circulating bovine prolactin assayed by radio-immuno assay. Experiments A.1 to A.3 thus demonstrate that reducing the molecular weight, $M_w$, or viscosity of the polylactide used in the manufacture of a composition reduces the biphasicity of polypeptide release, for polypeptides of low or medium molecular weight, or the initial delay in release of polypeptides of medium or high molecular weight, and achieves a continuous release of the polypeptide from $T_o$.

B. Ratio of lactide/glycolide in the polylactide

Compositions were manufactured in the form of implants containing 100 μg. (3% w/w) of the luliberin analogue ICI. 118,630 in polylactides of $M_w \sim 300{,}000$ but of different lactide/glycolide ratios. All of these formulations when tested in vivo in adult female rats exhibiting normal oestrous behaviour, gave biphasic release of the polypeptide, comprising release for about 6 days post-treatment, followed by a dead period, during which there was no significant polypeptide release. The length of this dead period decreased with decreasing lactide/glycolide ratio (L/G), as follows:

| L/G | Dead period (days) |
|---|---|
| 100/0 | no release |
| 75/25 | 51 |
| 67/33 | 34 |
| 50/50 | 15 |

This experiment thus indicates that a composition exhibiting a biphasic release of polypeptide can be improved in the direction of achieving continuous release by increasing the proportion of glycolide to lactide in the polylactide used, up to about 50C % glycolide.

C. Ratio of polypeptide to polylactide

Compositions in the form of implants were manufactured using different concentrations of the synthetic luliberin analogue, ICI.118,630, in a prior art 50/50 lactide/glycolide polylactide of $M_w \sim 200{,}000$, and tested in vivo in rats as described above. At 5% and 10% w/w incorporation, the release of polypeptide was biphasic, but at 15% and 20% incorporation, the biphasicity disappeared.

This experiment thus demonstrates that a polylactide of high molecular weight, which gives biphasic release of polypeptide when the polypeptide is incorporated only at low levels, can be used to make satisfactory continuous release formulations if the proportion of polypeptide is increased sufficiently.

D. Molecular weight distribution

A solution of a polymer blend of wide molecular weight distribution (polydispersity) was obtained by mixing solutions of a 50/50 D,L-lactide/glycolide polylactide of low $M_w$, (reduced specific viscosity of a 1 g./100 ml. solution in chloroform=0.115), (3 parts by weight) and a 50/50 D,L-lactide/glycolide polylactide of $M_w=200{,}000$, (intrinsic viscosity =1.08), (1 part by weight). Tetragastrin (1 part by weight) was added, and the mixture was cast to give a polylactide/tetragastrin composition containing 20% by weight of tetragastrin, and this was then moulded to give a slab 0.02cm. thick. The slab was placed in water at 37°C. and the release of tetragastrin was found to be continuous from $T_o$, and to continue for at least 44 days.

Polylactides of wide molecular weight distribution may be obtained either by mixing preformed polymers of different molecular weights, or by appropriate control of the polymerisation process in generally known manner, and such polylactides confer important advantages, for example the lower molecular weight polylactide species allow an essentially immediate release of some polypeptide, while the higher molecular weight polylactide species both extend the release period and slow down the overall rate of release of the polypeptide. In addition, the blending of low and high $M_w$ fractions modifies the water absorption characteristics of the polylactide in a parallel manner.

E. Thickness of the implant

E.1

A solution of 10% by weight of tetragastrin in a polylactide comprising equimolar proportions of D,L-lactic acid and glycolic acid units, and of $M_w \sim 15000$ was cast into films 0.02, 0.06 and 0.12 cm. thick. All three films showed continuous release of tetragastrin from $T_o$, and at 28 days, the three films had released respectively 85, 75 and 66% of their tetragastrin content.

E.2

The uptake of tritiated water from pH 7.4 buffer by slabs of polylactide comprising equimolar proportions of D,L-lactic acid and glycolic acid units of $M_w \sim 200{,}000$, and intrinsic viscosity=1.08 and of thickness 0.02, 0.06, 0.12 and 0.20 was measured by removing such slabs from the buffer solution successively after varying times of immersion, and measuring the tritium content by scintillation counting. After 5 weeks, the different thickness slabs had absorbed respectively 44, 20, 15 and 11% by weight of water.

These experiments show how the thickness of the implant can be used to control the absorption of water by, and thus the rate of release of polypeptide from, a composition of the invention, thicker implants releasing the polypeptide more slowly than thinner ones.

As indicated above the composition of the invention may be formulated as a solid composition for sub-dermal injection or implantation or as a liquid formulation for intramuscular or subcutaneous injection.

Suitable solid compositions for sub-dermal injection or implantation are, for example, rods, spheres, films or pellets, and cylindrical rods which can be injected through a hypodermic needle or trochar are preferred. Such compositions are manufactured by conventional techniques which are well known in the pharmaceutical art.

Preferred solid compositions of the invention, for polypeptides within different molecular weight ranges, are as shown in Table 1, and preferred compositions for specific polypeptides of particular interest are as shown in Table 2. Each entry in Tables 1 and 2 thus defines a further feature of this invention.

TABLE 1

| No. | Polypeptide M.W. | Polylactide Inherent Viscosity | Glycolide Lactide | % Polypeptide | Preferred % Polypeptide |
|---|---|---|---|---|---|
| 1. | <2000 | >0.5 | 0.5–3 | 5–50 | |
| 2. | <2000 | 0.2–0.5 | 0.2–3 | 5–50 | 10–30 |
| 3. | <2000 | <0.2 | 0–3 | 0.1–50 | |
| 4. | 1500–10,000 | 0.4–0.8 | 0.5–3 | 10–50 | 20–50 |
| 5. | 1500–10,000 | 0.15–0.4 | 0.2–3 | 5–30 | 10–30 |
| 6. | 1500–10,000 | <0.15 | 0–3 | 0.1–20 | 1–20 |
| 7. | 8000–30,000 | 0.15–0.4 | 0–3 | 0.1–50 | |
| 8. | 8000–30,000 | 0.1–0.15 | 0.7–3 | 10–50 | |
| 9. | 8000–30,000 | <0.1 | 0–3 | 0.1–50 | |

TABLE 2

| No. | Polypeptide | Polylactide Inherent Viscosity | Glycolide Lactide | % Polypeptide |
|---|---|---|---|---|
| 10. | Tetragastrin | >0.5 | 1–3 | 5–50 |
| 11. | Tetragastrin | 0.2–0.5 | 0.5–3 | 5–50 |
| 12. | Tetragastrin | <0.2 | 0–3 | 0.1–50 |
| 13. | ICI. 118630 | >0.5 | 0.8–3 | 5–50 |
| 14. | ICI. 118630 | 0.2–0.5 | 0.2–3 | 5–50 |
| 15. | ICI. 118630 | <0.2 | 0–3 | 0.1–50 |
| 16. EGF | | 0.4–0.8 | 0.5–3 | 10–50 |
| 17. EGF | | 0.15–0.4 | 0–3 | 0.1–50 |
| 18. Prolactin | | <0.15 | 0–3 | 0.1–50 |

Also as indicated above, the composition of the invention may also be formulated as a suspension for injection. Such suspensions may be manufactured by general techniques well known in the pharmaceutical art, for example by milling the polylactide/polypeptide mixture in an ultracentrifuge mill fitted with a suitable mesh screen, for example a 120 mesh, and suspending the milled, screened particles in a solvent for injection, for example propylene glycol, water optionally with a conventional viscosity increasing or suspending agent, oils or other known, suitable liquid vehicles for injection.

The continuous release of ICI.118630 from a suspension composition of the invention was demonstrated by comparing the dioestrous behaviour of normal mature female rats dosed subcutaneously with either a propylene glycol suspension of particles milled to 120-mesh size and containing 3% by weight of ICI.118630 in a polylactide comprising equimolar proportions of D,L-lactic acid and glycolic acid units, and a $M_w \sim 240,000$, (intrinsic viscosity=1.36), or with a saline solution of 100, 200 or 300µg. of ICI.118630 per animal. With the saline solutions, there was an immediate short period of dioestrus, but after 3 days post-dosing normal cyclicity was re-established. With the suspension composition of the invention, by contrast, the animals were substantially in dioestrus for about 40 days. Similar results were obtained with an injection formulation based on a mixture of 1% of ICI.118630 in a similar polylactide having an intrinsic viscosity of >0.5.

Thus, according to a further feature of the invention there is provided a suspension formulation comprising from 1 to 50% by weight of a solid formulation, which itself comprises from 0.1 to 50% by weight of an acid-stable polypeptide as herein defined and from 50 to 99.9% by weight of a polylactide wherein the ratio of glycolide to lactide units is 0 to 3 and which is either soluble in benzene and has an inherent viscosity (1 g./100 ml. solution in benzene) of less than 0.5 or is insoluble in benzene and has an inherent viscosity (1 g./100 ml. solution in chloroform or dioxan) of less than 4, which solid formulation has been reduced to fine particle size, together with from 50 to 99% by weight of a liquid carrier suitable for injection into mammals.

It is to be noted that, because of the reduced particle size of the polypeptide/polylactide in a suspension for injection, certain solid formulations, which are not suitable for implantation, are rendered useful when reduced to fine particle size and formulated as a suspension for injection. For example, the two particular suspension formulations referred to above both contain less ICI.118,630 than has been found acceptable for implantable formulations, as shown in Tables 1 and 2 above.

From the foregoing, it is clear that it is desirable to manufacture polylactides of a range of $M_w$, particularly of low to medium $M_w$ in the range up to 60,000, and of high polydispersity ($M_w/M_n$), these being particularly valuable in the compositions of this invention. The prior art relating to polylactides in general, and to copolymers containing lactic acid and glycolic acid units in particular, is silent as to the manufacture of such copolymers of low molecular weight, and as to methods of achieving high polydispersity in such copolymers. Indeed, it is inherent in the prior art disclosure of polylactides that they are generally of $M_w$ greater than about 30,000–60,000 (an inherent viscosity of greater than 0.5) and of low polydispersity, due to their manufacture under anhydrous conditions and without any added chain-stoppers. We have realised that, because of the different reactivities under polymerisation conditions of the cyclic dimers of lactic acid and glycolic acid, copolymers of high heterogeneity in respect of polymer species may be obtained by ring opening polymerisation of a mixture of the two cyclic dimers in the presence of chain-stopping agents, to give polylactides having an inherent viscosity of less than 0.5. The cyclic dimer of glycolic acid is the more reactive under polymerisation conditions, and thus the first copolymer molecules formed in the polymerisation are glycolic acid-rich. Consequentially, the later copolymer molecules formed are necessarily lactic acid-rich, thus producing a copolymer of lactic acid and glycolic acid of the desired high heterogeneity.

In addition, we control the polymerisation to produce copolymers in the desired low $M_w$ range by carrying out the ring opening copolymerisation of the mixed cyclic dimers in the presence of water, of lactic acid containing water, or of some other known chain growth regulator, in accordance with the general knowledge in the polymer art.

Suitable polymerisation catalysts are zinc oxide, zinc carbonate, basic zinc carbonate, diethylzinc, organotin compounds, for example stannous octanoate, tributylaluminium, titanium, magnesium or barium compounds, or litharge, and of these stannous octanoate is preferred.

The copolymerisation of the mixed cyclic dimers is otherwise carried out in conventional manner, known in the polymer art, as regards time and temperature.

Low molecular weight polylactides may also be obtained by copolymerisation of the hydroxy-acids themselves rather than the cyclic dimers. Although less heterogenerous polymers are obtained by this process, suitable matrices for continuous release of polypeptides may be obtained by mixing such polylactides of different compositions made by this method, or by mixing a polylactide made by this method with one or more polylactides made by ring opening polymerisation of the cyclic dimers.

Certain of the lactic acid/glycolic acid copolymers described herein are novel and form a further feature of this invention. Thus according to a further feature of the invention there is provided a heterogeneous polylactide comprising from 25 to 100% molar lactic acid units and from 0 to 75% molar of glycolic acid units, and which is either soluble in benzene and has an inherent viscosity (1 g./100 ml. solution in benzene) of less than 0.5, or is insoluble in benzene and has an inherent viscosity (1 g./100 ml. solution in chloroform or dioxan) of less than 4. By a "heterogeneous polylactide" we mean polylactides with a high degree of heterogeneity, in respect of glycolide-rich and lactide-rich molecules, or of high polydispersity, or blends of two or more different polylactides which differ in lactide/glycolide content and/or $M_w$, as hereinbefore described.

Whether or not a particular copolymer is heterogeneous or not, in this sense, may be readily determined from inspection of the 25MHz $^{13}$C nuclear magnetic resonance spectrum of the copolymer in, for example, deuterated dimethyl sulphoxide. In a homogeneous copolymer, such as is obtained in the prior art copolymerisation of lactic acid and glycolic acid monomers, the resonance of the glycolic acid unit carbonyl carbon, at $\delta = 166.0-166.2$ approximately, appears as two doublets, as a consquence of the four different, approximately equally probable molecular environments in which this carbon atom can exist, namely GĠG, LĠG, GĠL and LĠL (G=a glycolic acid unit, L=a lactic acid unit, and the asterisk indicates the glycolic acid unit under consideration). In a heterogeneous copolymer, on the other hand, such as is used in the present invention, the sequence LĠL is unlikely to occur, so that one of the doublet singnals in the spectrum of the homogeneous copolymer appears as a singlet. In fact, we find that in the spectrum of heterogeneous copolymers, this glycolic acid unit carbonyl carbon signal often appears as two singlets. Thus, a "heterogeneous copolymer" as herein defined is a copolymer for which the glycolic acid carbonyl carbon signal in the $^{13}$C n.m.r. appears as other than a pair of doublets.

The heterogeneity or homogeneity of lactic acid/glycolic acid copolymers can also be demonstrated by an examination of their degradation. Thus, when a copolymer is placed in pH 7.4 buffer at 37° C., removed periodically, dried and sampled, and the ratio of lactic acid to glycolic acid units in the samples is determined by n.m.r., for a heterogeneous copolymer, the ratio L/G increases with time, as the glycolic acid sequences hydrolyse preferentially. For a homogeneous copolymer, on the other hand, the ratio of L/G remains essentially constant as degradation progresses.

The lactic acid content of the copolymer is preferably in the racemic (D,L) form, or in the optically active L form.

According to a further feature of the invention there is provided a process for the manufacture of a novel copolymer of lactic acid and glycolic acid as defined immediately above, which comprises the ring opening copolymerisation of a mixture of the cyclic dimers of lactic acid and glycolic acid, optionally in the presence of a chain growth regulating agent.

A suitable chain growth regulating agent is, for example, water, lactic acid, glycolic acid or other hydroxy acids, alcohols or carboxylic acids generally.

The invention is illustrated but not limited by the following Preparations and Examples:

PREPARATION 1

Zinc oxide (16g.) was added to D,L-lactic acid (800g.) in a 2 1 3-necked round bottom flask-equipped with a stirrer, a thermometer, and a distillation head connected to a water condenser. The mixture was stirred and heated to about 135° C., at which temperature water started to distil over. Heating was continued for 8 hrs., during which time the temperature rose to about 190 °C. When distillation of water ceased, the pressure was reduced, and distillation was continued until solid began to collect in the condenser. At this stage the water condenser was replaced by an air condenser, and the residue was cooled and then distilled under high vacuum (2-8 mm. of mercury), the fraction (about 300 g.) distilling between 130° and 160° C. being collected, this being D,L-lactide (3,6-dimethyl-1,4-dioxan-2,5-dione), the cyclic dimer of D,L-lactic acid.

The crude D,L-lactide was crystallised from ethyl acetate (approximately 600 ml.) three times, and the recrystallised product was finally dried at 45 °C. under reduced pressure (2 mm. of mercury) for 24–48 hours, after which it had m.p. 124°–125° C.

PREPARATION 2

Glycolide (1,4-dioxan-2,5-dione), the cyclic dimer of glycolic acid, was prepared by the method described in Preparative Methods in Polymer Chemistry by W.R. Sorenson and T.W. Campbell, second edition, published by Interscience (1968), page 363. The crude glycolide was purified by three successive crystallisations from dry ethyl acetate, then dried at 45° C. under reduced pressure (2-8 mm. of mercury) for 24-48 hrs., m.p. 82°–84° C.

EXAMPLES 1 to 13

Polymers of D,L-lactide and glycolide were prepared as follows:

Pure dry D,L-lactide (Preparation 1), pure dry glycolide (Preparation 2) totalling 42 g., commercial D,L-lactic acid containing about 12% by weight of water, and 1 ml. of an 8% by weight solution of stannous octanoate in hexane, were placed in a pre-dried glass tube. The hexane was evaporated under reduced pressure, and the tube was heated at 160° C. for 6 hours with constant agitation if possible. The tube was cooled in powdered solid carbon dioxide, and the polylactide was removed, broken into small pieces and dissolved in chloroform (400 ml.). The chloroform solution was filtered, and the filtrate was poured into methanol (2 l.) to precipitate the polylactide, which was filtered off and dried under vacuum at 40° C. for 24 hours, then at 80° C. for 24 hours. All the polylactides so produced were soluble in chloroform and dioxan, and polylactides 1 to 9 in the following Table were soluble in benzene, but polylactides 10 to 13 were insoluble in benzene.

The following particular polylactides were prepared by this method:

| Ex. | D,L-Lactide (L) (g.) | Glycolide (G) (g.) | L/G Molar Proportion | D,L-Lactic acid | Intrinsic Viscosity | $M_w$ (approx.) |
|---|---|---|---|---|---|---|
| 1 | 42.0 | 0 | 100/0 | 0 | 1.385 | 440,000 |
| 2 | 33.5 | 9.0 | 75/25 | 0 | 1.084 | 400,000 |
| 3 | 32.4 | 8.7 | 75/25 | 920 μl. | 0.108* | low |
| 4 | 30.0 | 12.1 | 67/33 | 0 | 0.97 | 370,000 |
| 5 | 30.0 | 12.1 | 67/33 | 0 | 0.94 | 214,000 |
| 6 | 30.0 | 12.1 | 67/33 | 30 μl. | 0.67 | 107,000 |
| 7 | 30.0 | 12.1 | 67/33 | 60 μl. | 0.51 | 63,000 |
| 8 | 30.0 | 12.1 | 67/33 | 120 μl. | 0.37 | 33,000 |
| 9 | 30.0 | 12.1 | 67/33 | 920 μl. | 0.121* | low |
| 10 | 23.0 | 18.5 | 50/50 | 0 | 1.045 | 300,000 |
| 11 | 23.0 | 18.5 | 50/50 | 400 μl. | 0.25 | 15,200 |
| 12 | 23.0 | 18.5 | 50/50 | 920 μl. | 0.126* | low |
| 13 | 23.0 | 18.5 | 50/50 | 1380 μl. | 0.108* | low |

$M_w$ are relative to polystyrene standard
*are reduced specific viscosities of a 1g./100 ml. solution in chloroform.

Alternatively, the lactide, glycolide and lactic acid if present, may be heated at 160° C. and 0.08 g. of stannous octanoate then added to initiate the polymerisation.

EXAMPLE 14

A polylactide comprising equimolar proportions of glycolic acid and D,L-lactic acid units, and having an intrinsic viscosity of 1.36 (50 mg.) was dissolved in dioxan (1 ml.), and 50μl. of a solution of ICI.118630,

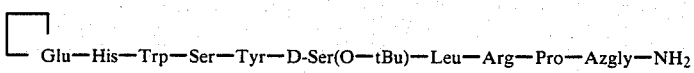
Glu—His—Trp—Ser—Tyr—D-Ser(O—tBu)—Leu—Arg—Pro—Azgly—NH$_2$ (233 mg. per ml. of the acetate salt, equivalent to 200 mg. per ml. of base) in distilled water was added. The resultant hazy solution was cast as a film, the solvents were evaporated in a stream of nitrogen in the dark, and the film was dried at 40° C. under reduced pressure (0.02 mm. of mercury) for 48 hours. The mixture, containing ~17% by weight of ICI.118630 in the polylactide was homogenized by three successive compression mouldings at 110° C. for 10 seconds, and was finally compression moulded into implants 0.038 cm. thick, each weighing 1.5 mg. and containing 309±7 μg. (~17% by weight) of ICI.118630.

The continuous release of ICI.118630 from such implants was demonstrated by placing them in female rats exhibiting normal oestrous behaviour. After implantation, the rats went into a period of dioestrus, detected by the lack of cornified vaginal smears, lasting from 31 to 40 days, thus indicating that ICI.118630 was being continuously released during that period.

The process described above was repeated, using 50 μl. of ICI.118630 acetate solution (150 mg. of pure peptide per ml. of water) and implants were made similarly, weighing 2 mg., containing 3C6±6+μg. of ICI.118630 (13% by weight), and 0.038 cm. in thickness. In the rat oestrus test described above, these implants released ICI.118630 continuously over a period of 30 to 38 days, as evidence by the period of dioestrus in the rats.

For use in human therapy, implants containing 1 to 100 mg. of ICI 118630 (5–50% by weight), weighing 2 mg.–1 g., and in the form of cylindrical rods suitable for implantation by trochar, were manufactured by the process described above.

EXAMPLE 15

The process described in Example 14 was repeated, but using polylactides comprising equimolar proportions of D,L-lactic acid and glycolic acid units, and having intrinsic viscosities of 0.33 and 0.25, instead of 1.36, to prepare implants containing 10% by weight of ICI.118630, weighing about 3 mg., and 0.08 cm. thick.

These implants were placed in female rats (5 per group) which, prior to implantation, exhibited regular oestrous behaviour. The implants prepared from polylactide of intrinsic viscosity 0.33 exhibited an induction period of 5 days followed by a dioestrus period of about 26 days; and the implants prepared from polylactide of intrinsic viscosity 0.25 exhibited an induction period of 3–4 days, followed by a dioestrus period of about 25 days.

Similar implants, but containing 20% by weight of ICI.118630 were prepared in the same way, and these exhibited a similar dioestrus period, but no induction period, in the rat test described above.

For use in human therapy, implants containing 1 to 100 mg. of ICI.118630 (5–50% by weight), weighing 2 mg.–1 g., and in the form of cylindrical rods suitable for implantation by trochar were manufactured similarly.

EXAMPLE 16

The process described in Example 14 was repeated, using a polylactide comprising equimolar proportions of D,L-lactic acid and glycolic acid units, and having intrinsic viscosity of 1.36, to prepare mixtures of ICI.118630 and polylactide containing 3% and 1% by weight of ICI.118630. The mixture was micronised at room temperature in an ultracentrifuge mill fitted with a 120-mesh screen, and the micronised particles were suspended in propylene glycol for injection at a concentration of 100 mg. per ml.

Female rats showing regular oestrous behaviour were injected sub-cutaneously with 0.1 ml. of the 3% by weight propylene glycol suspension described above, or with 0.3 ml. of the 1% suspension. Both groups were monitored, by examining vaginal smears daily for cornification, and exhibited occasional cornified smears up to 20 to 24 days after dosing, followed by a clear dioestrus period up to days 38 to 42 after dosing, thus demonstrating continuous release of ICI.118630 over that period.

EXAMPLE 17

Tetragastrin hydrochloride, (Trp-Met-Asp-Phe-NH$_2$HCl), (200 mg.) was dissolved in a mixture of dioxan (9 ml.) and water (1 ml.), and to the solution was added a polylactide as described in Example 11 (1.8 g.). The mixture was cast as a film, and the solvents were evaporated in a stream of nitrogen. The resulting film was dried under reduced pressure (0.02 mm. of mercury) at 40° C. for 48 hours, then homogenised by three successive compression mouldings at 80° C. for 10 seconds, and moulded to give films of thickness 0.02, 0.06 or 0.12 cm., each weighing about 80 mg.

The release of tetragastrin was measured by placing a film in distilled water, removing a sample of the distilled water daily, replacing all the remaining distilled water by fresh, and measuring the ultraviolet absorption of the daily samples at 277 nm. The following results were obtained, which demonstrated continuous release of tetragastrin from films of all three thicknesses:

| Time(days) | Cumulative % Tetragastrin Released | | |
|---|---|---|---|
| | 0.02 cm. Film | 0.06 cm. Film | 0.12 cm. Film |
| 1 | 9.6 | 5.6 | 4.0 |
| 4 | 14.9 | 10.5 | 9.0 |
| 7 | 20.3 | 13.9 | 11.7 |
| 9 | 25.3 | 17.7 | 14.8 |
| 11 | 33.1 | 22.6 | 19.4 |
| 14 | 48.6 | 33.2 | 28.1 |
| 17 | 61.9 | 45.9 | 40.5 |
| 21 | 74.7 | 59.8 | 53.2 |
| 24 | 81.8 | 68.1 | 60.2 |
| 28 | 85.2 | 74.9 | 66.4 |
| 31 | 86.9 | 77.7 | 70.9 |
| 36 | 88.5 | 82.5 | 77.5 |
| 39 | 89.2 | 85.1 | 82.6 |

EXAMPLE 18

Tetragastrin hydrochloride (40 mg.) was dissolved in aqueous dioxan (1:9 by volume), and added to a solution of:

(a) a polylactide comprising equimolar proportions of D,L-lactic acid and glycolic acid units, and having a reduced specific viscosity of 0.115 (as a 1 g./100 ml. solution in chloroform), (120 mg.), and (b) a polylactide comprising equimolar proportions of D,L-lactic acid and glycolic acid residues, and having an intrinsic viscosity of 1.08 (40 mg.), in dioxan (2 ml.). The mixed solutions were cast as a film, as described in Example 14, and moulded as implants weighing about 50 mg., and 0.02 cm. thick.

The release of tetragastrin from these implants was measured by the procedure described in Example 17, and the following results showing continuous release were obtained:

| Time(days) | Cumulative % Tetragastrin Released |
|---|---|
| 1 | 0.6 |
| 2 | 1.0 |
| 3 | 1.6 |
| 4 | 2.7 |
| 7 | 8.6 |
| 10 | 17.2 |
| 14 | 29.4 |
| 18 | 43.1 |

-continued

| Time(days) | Cumulative % Tetragastrin Released |
|---|---|
| 23 | 56.3 |
| 28 | 64.9 |
| 32 | 71.2 |
| 36 | 79.0 |
| 39 | 83.9 |
| 44 | 90.5 |

EXAMPLE 19

A polylactide comprising equimolar proportions of D,L-lactic acid and glycolic acid units, and having an inherent viscosity of 0.11 as a 1 g./100 ml solution in chloroform, (50 mg.), was dissolved in dioxan (1 ml.) and a solution of mouse epidermal growth factor (EGF, 0.05 mg.) in water (0.05 ml.) was added. The mixture was cast as a film on polytetrafluoroethylene cloth, and the solvent was removed in a stream of nitrogen in the dark. The film was dried at 60° C. under reduced pressure (0.8 mm. of mercury) for 48 hours. The film was then compression moulded at 120° C. for 10 seconds to give implants 0.02 cm. thick, weighing 10 mg.

The implants were each placed in a black vial at 37° C. with 1 ml. of McIlvain's buffer (pH 7.4), (Documenta Geigy, Scientific Tables, edited by K.Diem and C. Leutner, published by J. R. Geigy SA, Basle, Switzerland, 7th Edition, 1970, page 280), containing 0.02% by weight of sodium azide. The buffer was removed daily, and replaced with fresh, and the EGF released into the buffer by the implant was measured by radio-immuno assay, which demonstrated that release started immediately, and continued for at least 2 weeks releasing 100–200 µg. per day.

EXAMPLE 20

A polylactide comprising equimolar proportions of D,L-lactide and glycolide and having a reduced specific viscosity (1 g./100 ml. solution in chloroform) of 0.11, (400 mg.), was dissolved in dioxan (2 ml.), and a solution/suspension of bovine prolactin (100 mg.) in distilled water (0.5 ml.) was added, with vigorous agitation. The mixture was poured onto a polytetrafluoroethylene cloth, and dried, first in a stream of nitrogen and then under reduced pressure (0.01 mm. of mercury) at 40° C. for 24 hours. The heterogeneous mixture thus obtained was homogenised by four successive compression mouldings at 60° C., and then moulded into a slab 0.2 cm. thick, from which implants weighing 60 mg. were excised.

The implants were place subcutaneously into adult female rats, which were then periodically bled from the tail, and the prolactin in the blood samples thus obtained was measured by radio-immune assay. A placebo group, receiving no prolactin in the implant, was similarly assayed, and the levels of circulating prolactin compared. The following results were obtained:

| Time | Plasma level of bovine prolactin (µg./ml.) | |
|---|---|---|
| | Placebo group | Treatment group |
| 1 | 0.38 | 24.7 |
| 2 | 0.45 | 105.9 |
| 6 | 0.54 | 7.7 |
| 9 | 0.72 | 17.8 |
| 13 | 0.52 | 65.4 |
| 16 | 0.56 | 89.7 |
| 20 | 0.75 | 288 |
| 23 | 0.81 | 142 |

-continued

| | Plasma level of bovine prolactin (μg./ml.) | |
|---|---|---|
| Time | Placebo group | Treatment group |
| 26 | 0.84 | 562 |
| 42 | 1.25 | 1250 |

EXAMPLE 21

The process described in Examples 1-13 was repeated, except that the polylactide was dissolved in dioxan instead of in chloroform and similar polylactides were obtained.

EXAMPLES 22-29

The process described in Examples 1-13 was repeated, except that the polylactide was dissolved in glacial acetic acid, and the glacial acetic acid solution thus obtained was added dropwise to methanol in order to precipitate the polylactide, which was filetered off and dried under vacuum at 40° C. for 24 hours, then at 80° C. for 24 hours.

The following particular polylactides were prepared by this method:

| Ex | D,L-lactide (L) (g) | Glycolide (G) (g) | L/G Molar proportion | D,L-Lactic acid | Intrinsic Viscosity | Mw. (approx.) | stannous octanoate |
|---|---|---|---|---|---|---|---|
| 22 | 33.3 | 26.7 | 50/50 | 360 μl | 0.234 | 13,500 | 93 μl |
| 23 | 11.1 | 8.9 | 50/50 | 120 μl | 0.243 | 14,450 | 31 μl |
| 24 | 11.1 | 8.9 | 50/50 | 120 μl | 0.265 | 16,800 | 31 μl |
| 25 | 111.0 | 89.0 | 50/50 | 1.2 ml | 0.257 | 15,850 | 0.31 ml |
| 26 | 111.0 | 89.0 | 50/50 | 1.2 ml | 0.239 | 14,200 | 0.31 ml |
| 27 | 88.8 | 71.2 | 50/50 | 0.96 ml | 0.262 | 16,600 | 0.25 ml |
| 28 | 22.2 | 17.8 | 50/50 | 1.38 ml | 0.09* | | 62 μl |
| 29 | 20.0 | — | 100/0 | 0.12 ml | 0.260 | 16,200 | 31 μl |

*Inherent viscosity as 1 gm./100 ml. solution in chloroform.

EXAMPLE 30

A polylactide comprising equimolar proportions of glycolic acid and D,L-lactic acid units and having an intrinsic viscosity of 0.25 was dissolved in glacial acetic acid, and the solution was freeze-dried. The freeze dried powder (540.7 mg.) and ICI 118630 (142.1 mg.) of the acetate salt (equivalent to ≯ 124 mg. of base) were dissolved in 6.8 ml. of acetic anhydride-free glacial acetic acid and freeze dried for 24 hrs. (The glacial acetic acid was refluxed for 2 hrs. with 1% water to remove the acetic anhydride): The freeze dried product was extruded under pressure at 70° C. to a 1 mm. diameter rod, from which implants of the required weight were cut. The implants were dissolved in an appropriate solvent, for example acetonitrile, and assayed for drug content and purity. Implants were shown to contain 16.1% w/w pure 118630 base.

Release of 118630 was evaluated by immersing implants weighing approximately 10 mg. in McIlvains pH 7.4 buffer at 37° C. ICI 118630 was released continously for at least 5 weeks.

In a further experiment, implants weighing approximately 390 μg., 860 μg., 1500 μg., 3000 μg and ~6000 μg were implanted subcutaneously in groups of adult, regularly cycling female rats. In the 28 days following implantation, animals were essentially free of oestrus intervals showing that active drug was released continuously over this period.

EXAMPLE 31

A solution of ICI 118630 acetate salt was prepared by dissolving 170.8 mg. of ICI 118630 acetate in 5 ml. of acetic anhydride-free glacial acetic acid. (The glacial acetic acid was fluxed for 2 hrs. with 1% water to remove acetic anhydride). This solution was shown by high pressure liquid chromatography (HPLC),to contain 25.21 mg. of ICI 118630 base per ml. 442.5 mg. of polylactide (prepared as in Example 25 was dissolved in 4.5 ml. of the acetic acid solution, and the resulting solution was freeze dried for 25 hrs. The freeze dried product was extruded under pressure at 74° C. to a 1 mm. diameter rod, from which implants of the required weight were cut. The implants were dissolved in an appropriate solvent, such as acetonitrile, and the resulting solution was analysed by HPLC. The implants were shown to contain 20% w/w pure 118630 base.

EXAMPLE 32

A polylactide comprising equimolar proportions of D,L-lactic acid and glycolic acid units and having a reduced specific viscosity of 0.126 (1 g./100 ml. solution in chloroform), (240 mg.), was dissolved in glacial acetic acid (5 ml.) and a solution of tetragastrin hydrochloride (60 mg.) dissolved in glacial acetic acid (5 ml.) was added with vigorous agitation. The solution was freeze dried for 24 hrs. and the resultant solid was compression moulded at 50° C. for 20 seconds to give implants 0.2 cm thick and weighing 35-40 mgs.

The above procedure was repeated with the following polymers:

(a) a polylactide comprising 67 mole % of D,L-lactic acid and 33 mole % glycolic acid units and having a reduced specific viscosity of 0.121 (1 g./100 ml. solution in chloroform).

(b) a polylactide comprising 75 mole % of D,L-lactic acid and 25 mole % glycolic acid units and having a reduced specific viscosity of 0.108 (1 g./100 ml. solution in chloroform).

(c) a polylactide comprising 100% of D,L-lactic acid and having a reduced specific viscosity of 0.100 (1 g./100 ml. solution of chloroform).

The release of tetragastrin form these implants was measured by the procedure described in Example 17, and the following results were obtained:

| | Cumulative % Tetragastrin released | | | |
|---|---|---|---|---|
| Time (days) | 50% D,L-lactide 50% glycolide | 67% D,L-lactide 33% glycolide | 75% D,L-lactide 25% glycolide | 100% D,L-lactide |
| 1 | 6.0 | 1.0 | 1.7 | 1.9 |
| 3 | 12.9 | 2.1 | 3.2 | 3.0 |
| 7 | 23.3 | 7.1 | 8.0 | 5.1 |

| Time (days) | Cumulative % Tetragastrin released | | | |
|---|---|---|---|---|
| | 50% D,L-lactide 50% glycolide | 67% D,L-lactide 33% glycolide | 75% D,L-lactide 25% glycolide | 100% D,L-lactide |
| 9 | 27.2 | 12.2 | 11.6 | 6.5 |
| 11 | 30.3 | 20.2 | 15.8 | 8.2 |
| 15 | 36.7 | 40.0 | 27.0 | 14.0 |
| 17 | 39.3 | 45.0 | 29.7 | 17.9 |
| 21 | 44.5 | 51.8 | 35.1 | 25.5 |
| 24 | 49.6 | 55.6 | 37.9 | 30.4 |
| 28 | 58.8 | 59.6 | 41.1 | 36.1 |
| 31 | 68.8 | 62.3 | 42.8 | 40.1 |
| 35 | 81.5 | 67.3 | 45.0 | 45.6 |
| 39 | 91.0 | 74.3 | 47.6 | 50.7 |
| 42 | 95.9 | 81.9 | 50.6 | 55.3 |
| 46 | 96.5 | 89.1 | 55.5 | 60.4 |
| 49 | 97.5 | 93.2 | 60.0 | 65.2 |
| 53 | | 95.4 | 64.8 | 70.0 |
| 56 | | 96.3 | 68.6 | 73.6 |
| 59 | | 97.0 | 73.1 | 77.8 |
| 63 | | 97.2 | 77.1 | 81.5 |
| 70 | | | 82.7 | 86.1 |
| 74 | | | 85.0 | 87.5 |
| 84 | | | 90.4 | 89.5 |

These results show that continuous release of tetragastrin is obtained using low molecular weight polylactides and that duration of release is determined by the composition of the hydrolytically unstable polyester.

EXAMPLE 33

A polylactide comprising equimolar proportions of D,L-lactic acid and glycolic acid units and having an inherent viscosity of 0.126 (as a 1 g/100 ml. solution in chloroform) (9.5 mg.), was dissolved in distilled dioxan (0.25 ml.) and a solution of mouse epidermal growth factor (EGF 0.5 mg.) in distilled water (0.1 ml.) was added. The mixture was cast as a film on polytetrafluoroethylene cloth, and the solvent was removed in a stream of nitrogen, in the dark. The film was dried at 40° C. under reduced pressure (0.01 mm. of mercury) for 48 hrs. The film was then compression moulded at 70° C. for 10 seconds to an implant 0.02 cm. thick, weighing about 9 mgs. A placebo implant was also prepared.

The samples were implanted subcutaneously into carotid cannulated guinea pigs, blood samples taken periodically and the plasma EGF levels were measured by radio-immuno assay.

Raised plasma EGF levels were observed from Day 3 and continued for at least 1 week.

Similar implants were prepared as described above, but using a polylactide comprising equimolar proportions of D,L-lactic acid and glycolic acid units and having an intrinsic viscosity of 1.06. Compression moulding of this implant was done at 120° C.

Implantation and plasma assays were done as described above, but raised plasma EGF levels were not observed until day 17 after implantation.

EXAMPLE 34

A polylactide comprising equimolar proportions of D,L-lactic acid and glycolic acid units and having an inherent viscosity of 0.093 as a 1 g./100 ml. solution in chloroform (40 mg.) was dissolved in anhydrous-free glacial acetic acid (1 ml.) and a solution of mouse epidermal growth factor (EGF, 8.15 mg.) in a mixture of water (0.5 ml.) and anhydride-free glacial acetic acid (3 ml.) was added. The solution was freeze-dried for 24 hrs. The resulting powder was then compression moulded at 50° C. to give an implant 2 mm.× 2 mm.× 10 mm. weighing 36.1 mg.

The sample was implanted subcutaneously into a cannulated cat, blood samples were taken periodically and the plasma EGF levels were measured by radio-immuno assay.

Raised plasma EGF levels were observed from day 3 and continued for at least 40 days.

EXAMPLE 35

Implants containing bovine prolactin were prepared as described in Example 20, but using:

(a) a polylactide (400 mg.) comprising equimolar proportions of D,L-lactic acid and glycolic acid units and having a reduced specific viscosity (1 g./100 ml. solution in chloroform) of 0.11, dissolved in 4 ml dioxan; and (b) a polylactide (400 mg.) comprising equimolar proportions of D,L-lactic acid and glycolic acid units and having an intrinsic viscosity of 1.06 dissolved in 4 ml. dioxan. This sample was moulded at 110° C.

Formulations (a) and (b) were each tested in vivo as described in Example 20. Formulation (a) released significant levels of plasma bovine prolactin from at least as early as day 4 and continued to release for at least 85 days, while formulation (b) released significant levels from at least as early as day 8 for at least 85 days.

What I claim is:

1. A pharmaceutical composition comprising (a) from 50% to 99.999% of a polylactide which is a polymer of lactic acid alone, a copolymer of lactic acid and glycolic acid wherein the ratio of glycolide to lactide units is from 0 up to 3:1, a mixture of such polymers, a mixture of such copolymers, or a mixture of such polymers and copolymers, the lactic acid being either in racemic or in optically active form, and such polyactide being either soluble in benzene and having an inherent viscosity of from 0.093 (1 g. per 100 ml. in chloroform) to 0.5 (1 g. per 100 ml. in benzene), or insoluble in benzene and having an inherent viscosity of from 0.093 (1 g. per 100 ml in chloroform) to 4 (1 g. per 100 ml in chloroform or dioxan), and (b) from 0.001% to 50% of a pharmacologically active polypeptide which has a molecular weight at least about the same as the molecular weight of tetragastrin, which is not significantly hydrolized under the conditions encountered within the composition during the period of use envisioned, and which contains four or more amino acid residues, said polypeptide being uniformly dispersed in said polylactide, which composition, when placed in an aqueous physiological-type environment absorbs water and exhibits two successive phases of release of polypeptide, the first phase being release by initial diffusion through aqueous polypeptide domains communicating with the exterior surface of the composition, and the second phase being release consequent upon degradation of the polylactide, characterized in that the diffusion phase and the degradation-induced phase overlap in time, said composition being further characterized by the fact that, when placed in an aqueous physiological type environment, water diffuses into the matrix and is partitioned between polypeptide and polylactide to form aqueous polypeptide domains, the said domains increasing with increasing absorption of water until the continuity of the said domains reaches a sufficient level to communicate with the exterior surface of the composition, whereupon polypeptide starts to be released from said composition by diffusion through aqueous polypeptide channels formed from said domains, which second phase continues until substantially all of the remaining polypeptide is released 2. A pharmaceutical composition as claimed in claim 1 wherein the acid-stable polypeptide is oxytocin, vasopressin, adrenocorticotrophic hormone (ACTH), epidermal growth factor (EGF), prolactin, luliberin or luteinizing hormone releasing hormone (LH-RH), insulin, somatostatin, glucagon, interferon, gastrin, tetragastrin, pentagastrin, urogastrone, secretin, calcitonin, enkephalins, endorphins, angiotensins, renin, bradykinin, bacitracins, polymyxins, colistins, tyrocidin, gramicidines, and synthetic analogues and pharmacologically-active fragments thereof.

3. A pharmaceutical composition as claimed in claim 1 comprising from 5 to 50% by weight of a polypeptide of molecular weight less than 2000 and from 50 to 95% by weight of a polylactide wherein the ratio of glycolide to lactide units is from 0.5 to 3, and which has an inherent viscosity of greater than 0.5.

4. A pharmaceutical composition as claimed in claim 1 comprising from 5 to 50% by weight of a polypeptide of molecular weight less than 2000, and from 50 to 95% by weight of a polylactide wherein the ratio of glycolide to lactide units is from 0.2 to 3, and which has an inherent viscosity of 0.2 to 0.5.

5. A pharmaceutical composition as claimed in claim 1 comprising from 0.1 to 50% by weight of a polypeptide of molecular weight less than 2000 and from 50 to 99.9% by weight of a polylactide, and which has an inherent viscosity of less than 0.2.

6. A pharmaceutical composition as claimed in claim 1 comprising from 10 to 50% by weight of a polypeptide of molecular weight 1,500 to 10,000 and from 50 to 90% by weight of a polylactide wherein the ratio of glycolide to lactide units is 0.5 to 3, and which has an inherent viscosity of 0.4 to 0.8.

7. A pharmaceutical composition as claimed in claim 1 comprising from 5 to 30% by weight of a polypeptide of molecular weight 1,500 to 10,000 and from 70 to 95% by weight of a polylactide wherein the ratio of glycolide to lactide units is 0.2 to 3, and which has an inherent viscosity of 0.15 to 0.4.

8. A pharmaceutical composition as claimed in claim 1 comprising from 0.1 to 20% by weight of a polypeptide of molecular weight 1,500 to 10,000 and from 80 to 99.9% by weight of a polylactide wherein the ratio of glycolide to lactide units is 0 to 3, and which has an inherent viscosity of less than 0.15.

9. A pharmaceutical composition as claimed in claim 1 comprising from 0.1 to 50% by weight of a polypeptide of molecular weight 8,000 to 30,000 and from 50 to 99.9% by weight of a polylactide, and which has an inherent viscosity of 0.15 to 0.4.

10. A pharmaceutical composition as claimed in claim 1 comprising from 10 to 50% by weight of a polypeptide of molecular weight 8,000 to 30,000 and from 50 to 90% by weight of a polylactide wherein the ratio of glycolide to lactide units is 0.7 to 3, and which has an inherent viscosity of 0.1 to 0.15.

11. A pharmaceutical composition as claimed in claim 1 comprising from 0.1 to 50% by weight of a polypeptide of molecular weight 8,000 to 30,000 and from 50 to 99.9% by weight of a polylactide, and which has an inherent viscosity of less than 0.1.

12. A pharmaceutical composition as claimed in claim 1 comprising from 5 to 50% by weight of the synthetic luliberin analogue Glu-His-Trp-Ser-Tyr-D-Ser-(O-tBu)-Leu-Arg-Pro-Azgly-NH2, molecular weight=1269, and from 50 to 95% by weight of a polylactide wherein the ratio of glycolide to lactide units is 0.8 to 3, and which has an inherent viscosity of more than 0.5.

13. A pharmaceutical composition as claimed in claim 1 comprising from 5 to 50% by weight of the synthetic luliberin analogue Glu-His-Trp-Ser-Tyr-D-Ser-(O-tBu)-Leu-Arg-Pro-Azgly-NH2, molecular weight=1269, and from 50 to 95% by weight of a polylactide wherein the ratio of glycolide to lactide units is 0.2 to 3, and which has an inherent viscosity of 0.2 to 0.5.

14. A pharmaceutical composition as claimed in claim 1 comprising from 0.1 to 50% by weight of the synthetic luliberin analogue Glu-His-Trp-Ser-Tyr-D-Ser-(O-tBu)-Leu-Arg-Pro-Azgly-NH2, molecular weight=1269, and from 50 to 99.9% by weight of a polylactide which has an inherent viscosity of less than 0.2.

15. A pharmaceutical composition as claimed in claim 1 comprising from 10 to 50% by weight of epidermal growth factor or urogastrone and from 50 to 90% by weight of a polyactide wherein the ratio of glycolide to lactide units is 0.5 to 3, and which has an inherent viscosity of 0.4 to 0.8.

16. A pharmaceutical composition as claimed in claim 1 comprising from 0.1 to 50% by weight of epidermal growth factor or urogastrone and from 50 to 99.9% by weight of a polyactide wherein the ratio of glycolide to lactide units is 0.3, and which has an inherent viscosity of 0.15 to 0.4.

17. A pharmaceutical composition in the form of a suspension for use in injection comprising from 1 to 50% by weight, of a solid formulation as claimed in claim 1, which itself comprises from 0.1 to 50% by weight of a polypeptide which is not significantly hydrolyzed under the conditions encountered within the composition during the period of use envisioned and from 50 to 99.9% by weight of a polylactide wherein the ratio of glycoline to lactide units is 0 up to 3:1 and which is either soluble in benzene and has an inherent viscosity (1 g./100 ml. solution in benzene) of less than 0.5 or is insoluble in benzene and has an inherent viscosity (1 g./100 ml. solution in chloroform or dioxan) of less than 4, which solid formulation has been reduced to fine particle size, together with from 50 to 99% by weight of a liquid carrier suitable for injection into mammals.

* * * * *

REEXAMINATION CERTIFICATE (1328th)
United States Patent [19]
Hutchinson

[11] B1 4,767,628

[45] Certificate Issued     Jul. 17, 1990

[54] CONTINUOUS RELEASE PHARMACEUTICAL COMPOSITIONS

[75] Inventor: Francis G. Hutchinson, Lymm, United Kingdom

[73] Assignee: Imperial Chemical Industries PLC, London, England

Reexamination Request:
No. 90/001,713, Feb. 8, 1989

Reexamination Certificate for:
Patent No.: 4,767,628
Issued: Aug. 30, 1988
Appl. No.: 68,760
Filed: Jun. 29, 1987

Related U.S. Application Data

[63] Continuation of Ser. No. 640,855, Aug. 15, 1984, abandoned, which is a continuation of Ser. No. 344,722, Feb. 1, 1982, abandoned.

[30] Foreign Application Priority Data

Feb. 16, 1981 [GB] United Kingdom ............. 8104734

[51] Int. Cl.$^5$ ................... A61K 9/26; A61K 9/32
[52] U.S. Cl. ............................. 424/426; 514/12; 514/13; 514/14; 514/15; 424/422; 424/423
[58] Field of Search ........................ 514/12-15; 424/422, 423, 426

[56] References Cited

U.S. PATENT DOCUMENTS

| | | | |
|---|---|---|---|
| 2,703,316 | 3/1955 | Schneider | 528/354 |
| 3,773,919 | 11/1973 | Boswell | 424/78 |
| 3,887,699 | 6/1975 | Yolles | 424/78 |
| 4,001,388 | 1/1977 | Shell | 424/438 |
| 4,011,312 | 3/1977 | Reuter | 424/78 |
| 4,033,938 | 7/1977 | Augert | 528/354 |
| 4,234,571 | 11/1980 | Nestor | 514/15 |
| 4,419,340 | 12/1983 | Yolles | 424/426 |

FOREIGN PATENT DOCUMENTS

| | | |
|---|---|---|
| 0021234 | 1/1981 | European Pat. Off. |
| 0025698 | 3/1981 | European Pat. Off. |
| 0026599 | 4/1981 | European Pat. Off. |
| 0052510 | 5/1982 | European Pat. Off. |
| 1332505 | 10/1973 | United Kingdom |
| 1351409 | 5/1974 | United Kingdom |
| 2008135 | 5/1979 | United Kingdom |
| 2034182 | 6/1980 | United Kingdom |

OTHER PUBLICATIONS

Tice et al., *Pharm. Tech. Conference*, Biodegradable Controlled-Release Parenteral Systems, 246, 247 and 255, 1984.
*Sustained and Controlled Release Drug Delivery Systems*, edited by J. R. Robinson, Marcel Dekker, Inc., New York, 1978, pp. 141, 142 and 151.
*Microcapsule Processing and Technology*, edited by J. Wade Van Valkenburg, Marcel Dekker, Inc., N.Y., 1979, pp. 1-5.
Acta Eur Fertil, II, 139-150 (1980), Beck.
Bull Parenteral Drug Assoc., 30, 306, Yolles.
Chem Abstracts (Same as Midl Macromol Monographs) 91, 9442g (1979), Wise.
Contraception, 8, 227-233 (1973), Jackanicz.
Contraception, 13, 373-384 (1976), Anderson.
Environ Sci Tech, 7, 955 (1973), Sinclair.
Journal of Bioengineering, 1, 25-32 (1976), Chang.
J. Biomed Mater Res 1, 43-57 (1971), Frazza.
J. Biomed Mater Res 11, 711-719 (1977), Miller.
J. Biomed Mater Res 3, 169-181 (1971), Kulkarni.
J. Biomed Mater Res 7, 155-166 (1973), Brady.
J Membrane Sci 7, 277-291 (1980), Sidman.
J Membrane Sci 7, 333-350 (1980), Langer.
J Oral Med 30, 5-7 (1975), Cutright.
J. Pharm Pharmacol 30, 686-689 (1978), Wise.
J. Pharm Pharmacol 32, 399-403 (1980), Wise.
J. Pharm Sci 68, 1534-1538 (1979), Pitt.
J. Polymer Sci 17, 2593-2599 (1979), Schindler.
J Steroid Biochem 2, 449-455 (1979), Benagiano.
J Steroid Biochem 6, 909-915 (1975), Nash.
Life Science 17, 1877-1885 (1975), Schwope.
Makromol Chem, Supplement 12, 25-38 (1985), Kricheldorf.
Midl Macromol Monographs (Same as CA 91 9442) 5, 75-89; 121-127 (1978), Wise.
Oral Surg Oral Med Oral Pathol 37, 142-145 (1974), Cutright.
Org Coat Plast Chem 42, 436-440 (1980), Mason.
Pharmacy International Aug 1986, Lee.
Polymer 20, 1459-1464 (1979), Gilding.
Res Frontiers in Fert Regulation 1, 1 (1980), Beck.
Res Monograph Ser Natl Inst Drug Abuse (U.S.) 4, 13-18 (1976), Schwope.
Biodegradable Polymers for Sustained Drug Delivery, Schindler in Continuing Topics in Polymer Science, II (1977), 251-289.
Continued Development of an Implantable Sustained Release System for the Prevention of Malaria, Gregory & Wise (Dynachim), U.S. Army Con. No. DAMD 17-24-C-412.
Drug Carriers in Biology and Medicine, ed G. Gregoriadis, (1979), (Wise et al), 237-244, 237-270.
Grendrisse der makromolekularen Chemie, Vollmaert (1962), 134-139.
Hydrolytic Degradation of Poly DL-(Lactide)-source & date unknown, 436-440.
Polyesters, Korshak & Vinogradova, Pergamon 1965, 215-217.
Polymeric Delivery Systems, Kostelnik 1978, paper by Wise 75.
Lewis, 7th International Symposium on Controlled Release of Bioactive Materials, Fort Lauderdale, 129-131 (1980).
Pitt, Drug Delivery Systems, NIH Bethesda, 1977, 141-192.

*Primary Examiner*—Fatemeh T. Moezie

[57] ABSTRACT

Pharmaceutical compositions, comprising a polylactide and a pharmacologically active, acid stable polypeptide, which when placed in an aqueous physiological environment release the polypeptide at an approximately constant rate in an essentially monophasic manner, with a minimal, or no induction period prior to the release; polylactides suitable for use in said compositions; and a method for the manufacture of such polylactides.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-17, dependent on an amended claim, are determined to be patentable.

1. A pharmaceutical composition [comprising] *for essentially monophasic continuous release of a polypeptide in the form of an implant or suspension for injection consisting essentially of* (a) from 50% to 99.999% of a polylactide which is a polymer of lactic acid alone, a copolymer of lactic acid and glycolic acid wherein the ratio of glycolide to lactide units is from 0 up to 3:1, a mixture of such polymers, a mixture of such copolymers, or a mixture of such polymers and copolymers, the lactic acid being either in racemic or in optically active form, and such polylactide being either soluble in benzene and having an inherent viscosity of from 0.093 (1 g. per 100 ml. in chloroform) to 0.5 (1 g. per 100 ml. in benzene), or insoluble in benzene and having an inherent viscosity of from 0.093 (1 g. per 100 ml in chloroform) to 4 (1 g. per 100 ml in chloroform or dioxan), and (b) from 0.001% to 50% of a pharmacologically active polypeptide which has a molecular weight *of* at least about the same as the molecular weight of tetragastrin, which is not significantly hydrolyzed under the conditions encountered within the composition during the period of use envisioned, and which contains four or more amino acid residues, said polypeptide being uniformly dispersed in said polylactide so that *some of the said polypeptide is present at the external surface of the composition*, which composition, when placed in an aqueous physiological-type environment absorbs water and exhibits two successive phases of release of polypeptide, the first phase being release by initial diffusion through aqueous polypeptide domains communicating with the exterior surface of the composition, and the second phase being release consequent upon degradation of the polylactide, characterized in that the diffusion phase and the degradation-induced phase overlap in time, said composition being further characterized by the fact that, when placed in an aqueous physiological type environment, water diffuses into the matrix and is partitioned between polypeptide and polylactide to form aqueous polypeptide domains, the said domains increasing with increasing absorption of water until the continuity of the said domains reaches a sufficient level to communicate with the exterior surface of the composition, whereupon polypeptide starts to be released from said composition by diffusion through aqueous polypeptide channels formed from said domains, which second phase continues until substantially all of the remaining polypeptide is released *over at least a week*.

* * * * *